United States Patent [19]

Ruscito et al.

[11] Patent Number: 5,573,501
[45] Date of Patent: Nov. 12, 1996

[54] ORTHOTIC WITH INDICIA BEARING LAYER

[76] Inventors: Joseph L. Ruscito, 414 Anthony Ave., Toms River, N.J. 08753; Frank P. Scarnati, 10 Hamilton Ct., Old Bridge, N.J. 08857

[21] Appl. No.: 117,820

[22] Filed: Sep. 7, 1993

[51] Int. Cl.⁶ ..................................... A61F 5/00
[52] U.S. Cl. ................... 602/7; 602/5; 602/27; 602/23; 428/246
[58] Field of Search ............................... 602/5–8, 20, 23, 602/27; 428/34.9, 36.1, 36.2, 36.91, 204, 206, 246, 252, 302; 156/148, 277; 264/222, 223

[56] References Cited

U.S. PATENT DOCUMENTS

| | | | |
|---|---|---|---|
| 4,126,719 | 11/1978 | Koyanagi et al. | 428/36.2 X |
| 4,442,833 | 4/1984 | Dahlen et al. | 602/8 |
| 4,446,858 | 5/1984 | Jordan . | |
| 4,554,912 | 11/1985 | Haberman . | |
| 4,718,179 | 1/1988 | Brown . | |
| 4,774,954 | 10/1988 | Ibrahim . | |
| 4,781,180 | 11/1988 | Solomonow . | |
| 4,793,330 | 12/1988 | Honeycutt et al. | 602/8 |
| 4,813,090 | 3/1989 | Ibrahim . | |
| 4,869,001 | 9/1989 | Brown . | |
| 4,893,671 | 1/1990 | Bartial et al. | 602/8 |
| 4,921,513 | 5/1990 | Parten | 156/277 X |
| 5,000,809 | 3/1991 | Adesko et al. . | |
| 5,088,484 | 2/1992 | Freeman et al. | 602/8 X |
| 5,121,742 | 6/1992 | Engen . | |
| 5,242,720 | 9/1993 | Blake | 428/36.2 X |

FOREIGN PATENT DOCUMENTS

| | | | |
|---|---|---|---|
| 9304709 | 3/1993 | WIPO | 602/6 |

OTHER PUBLICATIONS

JOF Enterprises, Inc., Decorative Healthwear "Wear It Out In Style" product literature, copyright 1992.
The Philadelphia Inquirer article: "For many reasons, today's children feel no disgrace in wearing braces", p. G4, Jul. 7, 1993.
Orthopedic Technology, Inc., Custom functional knee orthosis product literature, date unknown.

*Primary Examiner*—Linda C. Dvorak
*Attorney, Agent, or Firm*—Robert F. Zielinski

[57] ABSTRACT

A laminated, plastic orthotic device custom fitted to a wearer's extremity, typically a leg, wherein the orthotic includes a indicia bearing layer viewable on the outer surface of the orthotic. In one preferred embodiment, the device is fabricated from multiple layers of woven, reinforced and non-reinforced fabrics, adhesives, curable plastic resins and an image bearing layer. In other preferred embodiments, the device is fabricated of thermosetting plastic materials and an image bearing layer. The image layer may be comprised of woven fabric or non-woven materials which include drawings, insignias, photographs, textures or combinations thereof.

10 Claims, 3 Drawing Sheets

ORTHOTIC WITH INDICIA BEARING LAYER

FIELD OF THE INVENTION

This invention relates to orthotic devices and, more specifically, to laminated plastic orthoses having an indicia or image bearing layer integrally formed therein and to the method of manufacturing these devices.

BACKGROUND OF THE INVENTION

Orthotics is the branch of medical and mechanical sciences dealing with bracing and straightening weak or ineffective joints or muscles by the use of braces or supports. Orthotic devices are typically worn by individuals with physical limitations that have been acquired or that are congenital and are particularly worn by those individuals with physical limitations arising from neurological disorders occurring from cerebral palsy, multiple sclerosis, cerebral vascular accidents, club foot, spinabifida, and the like. In cases involving the leg or foot, treatment often involves the custom manufacture of orthotic devices which are worn either attached to or inside a patient's shoe and which extend upwardly on the outer surface of the calf and typically, over the patient's clothing. These devices help minimize physical discomfort for patients suffering from structural and/or physical deficiencies in their feet or legs.

In many instances, persons suffering with the above neurological disorders often develop marked deformities in the lower and upper extremities. In many instances the lower extremity deformity that results is classified as Spastic Equinovarus. Spasticity and its accompanying deformity of the lower limb severely reduces the ambulatory capacity of the individuals suffering from these disorders. Moreover, the deformity of the foot/ankle complex has traditionally been the most difficult to correct via orthotic devices, physical medicine, surgical intervention and medications.

The use of orthotic devices to help support and control joints of the lower extremities is an extremely important part of medical rehabilitation. Despite this importance, however, the development of lower extremity orthotic devices has experienced few major breakthroughs. For example, traditional orthotic devices consisting of metallic supports and leather and/or fabric straps are awkward and cumbersome, particularly for patients with generalized motor weakness. Most of these devices are heavy, unattractive and must be permanently attached to the wearer's shoes. Furthermore, these devices tend to cause damage to clothing due to frictional wear, rough edges and pinching joints.

Key to any therapeutic endeavor is patient compliance with the prescribed therapy. This is particularly true with orthotic devices which achieve their benefits only after they are properly and consistently worn over an extended period of time. With younger patients, and especially those children afflicted with cerebral palsy, the physical challenges associated with the disorder are often over shadowed by the psychological trauma of wearing the prescribed orthotic. In many instances a child must not only bear the burden of the physical handicap, but the stigma of having to wear an orthotic device; devices which call attention not only to the disorder of the individual but, more often, to the apparatus itself. The orthotics of the past were particularly egregious in this regard and in many cases patients would either forego wearing the prescribed orthotic or would preferentially engage in physical activities which did not require wearing the orthotic. The net result is, of course, that the orthotic cannot perform its intended function, and the patient realizes little or no appreciable benefit from a device which is under-utilized.

In the past two decades, new materials, particularly plastics and composite materials have become recognized as generally suitable replacements for the steel, aluminum and other metals formerly used to construct orthotic devices. Moreover, the use of these materials in orthotics allowed orthotists to consider new design concepts, resulting in lighter, less cumbersome and slightly more visually acceptable devices. For example, research at the Texas Institute for Rehabilitation and Research by Engen lead to the development of a molded polypropylene ankle-foot orthotic device (AFO) which is worn inside the shoe. This AFO eliminated the mechanical ankle joint and brace shoe attachment of conventional braces and allowed the user freedom to wear the device with his or her own shoe (Engen, Orthotics and Prosthetics 26 (4):1–5 1972).

Other plastic and plastic/composite orthotic therapeutic devices are also known. For example, U.S. Pat. No. 4,554,912 to Haberman is directed to a plastic orthotic therapeutic device for the treatment of varus or foot inversion and equinus or foot drop. The orthotic is made up of light weight, hygienic polypropylene and may be worn inside the patient's shoe.

U.S. Pat. No. 4,446,856 to Jordan also relates to a orthotic device which includes a boot for immobilizing the ankle and foot and holding the ankle and foot in a neutral position of maximal joint concurrency.

U.S. Pat. No. 5,121,742 to Engen relates to a lower extremity orthotic device including thermoplastic inner and outer side members in a thermoplastic ankle-foot orthotic member for a standing frame lower extremity orthotic apparatus.

While plastic orthotics have certain advantages in that they are often lighter in weight, less cumbersome, are mass manufacturable and are modifiable after fabrication to ensure proper fit, a drawback of orthotics in general, and even with respect to the plastic orthotics is the lack of any cosmetic appeal. In short, orthotic devices are generally unattractive; so much so that they cause attention to be drawn to the disability of the wearer rather than his or her abilities.

From the foregoing, it can be seen that it would be advantageous to provide an orthotic device which may be made more cosmetically appealing while still providing the beneficial effects associated with its use. It can also be seen that it would be desirable to provide an orthotic device which can be fabricated using readily available technologies. Finally, it will be appreciated that it would be desirable to provide an orthotic device which would allow the wearer the opportunity to express his or her own stylistic preferences or which may be adapted to suit the wearer's fashion needs.

It is an object of the present invention to provide a comfortable, effective and cosmetically appealing orthosis.

It is another object of the present invention to provide a lightweight, plastic, laminated orthosis which has a visible indicia bearing layer.

It is yet another object of the present invention to provide an orthosis which may bear a variety of indicia and which may be fabricated using currently available technologies.

It is still another object of the present invention to provide a cosmetically appealing orthosis which may be easily and inexpensively fabricated.

BRIEF SUMMARY OF THE INVENTION

The present invention achieves these and other advantages by providing a lightweight, plastic orthotic device which has integrally formed therein, an image which is viewable on the outer surface of the orthotic. The practice of the process of the present invention results in the production of a unique orthotic structure. In one embodiment, the orthotic is fabricated of woven reinforced and non-reinforced fabrics and curable thermosetting plastic materials and on which the outer surface of the orthotic can be permanently decorated with an image. The image may be carried on a woven or non-woven layer, which may be preferably covered by at least one outer layer of a substantially transparent woven material and which is embedded in the clear, curable plastic material which simultaneously provides a protective covering for the image layer and which does not interfere with the visibility of the image.

In another embodiment, where the orthotic is comprised of thermoplastic material, one obtains an orthotic having the strength and the ease of fabrication associated with thermoplastics with a laminated image layer permanently affixed thereto. In these embodiments, an un-laminated thermoplastic orthotic is first prepared by rough-sanding its outer surface. A polyester based adhesive is then applied and allowed to dry. The orthotic may then have the image bearing layer applied. The image bearing layer preferably is covered by at least one outer layer of a substantially transparent woven material. These layers are then coated with a clear, curable plastic material which simultaneously provides a protective covering for the image layer but does not interfere with the visibility of the image.

In other preferred embodiments, the orthotic may have integrally formed therein an outer surface which may have a textured surface or raised appearance which provides a visually appealing effect and which may be further enhanced by an underlying image layer.

The above description, as well as further objects, features and advantages of the present invention, will be more fully appreciated by reference to the following detailed description of the presently preferred, but nonetheless illustrative, embodiments in accordance with the present invention when taken in accordance with the accompanying drawings.

DETAILED DESCRIPTION OF THE PREFERRED EMBODIMENTS

Figure 1:
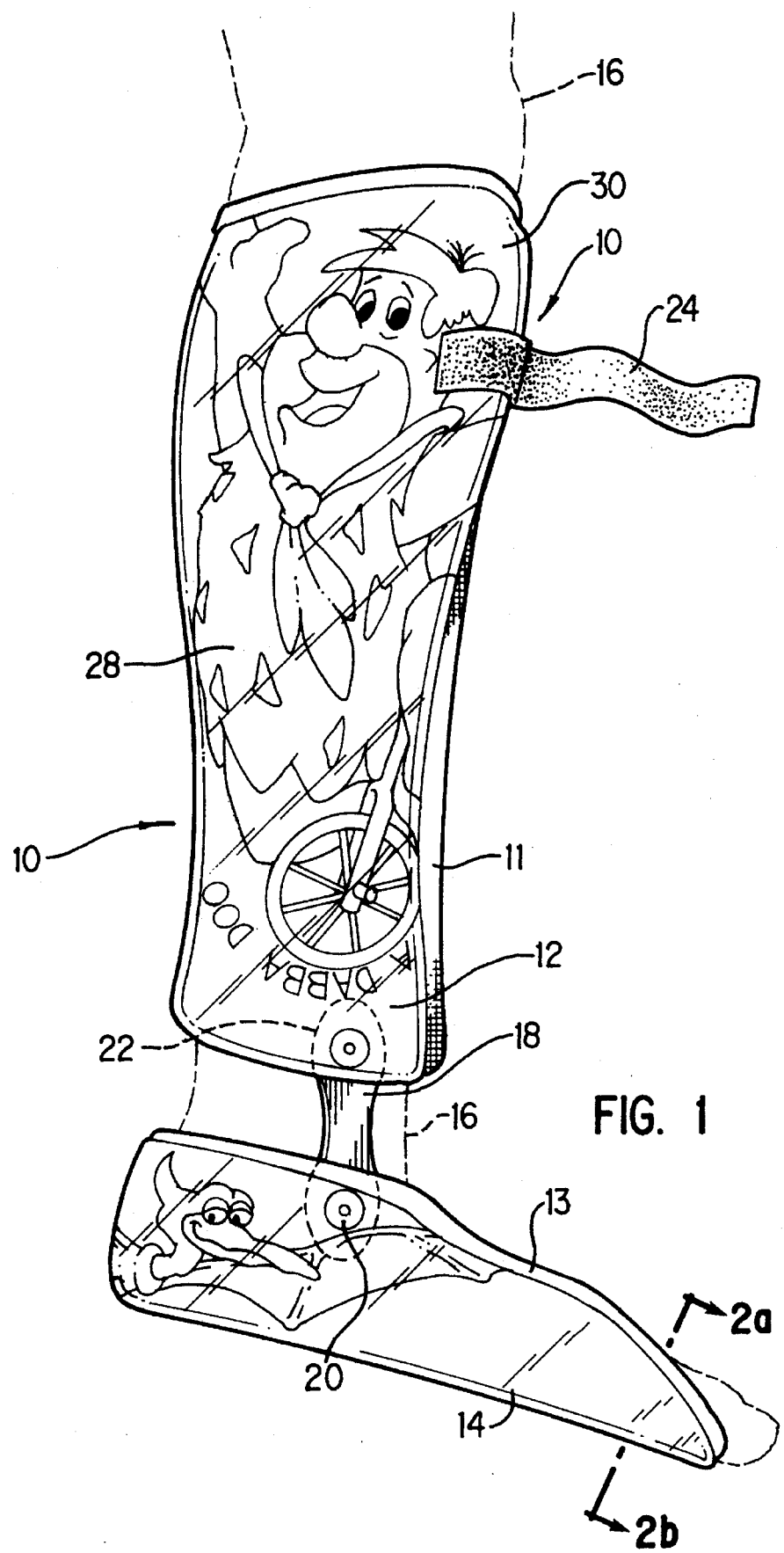
FIG. 1—Is a pictorial illustration of one preferred embodiment of an ankle-foot orthosis of the present invention.

With reference to FIG. 1, one embodiment of the invention is illustrated therein and it will be generally seen to include a lower ankle-foot orthotic device designated by the reference numeral 10. The plastic orthotic therapeutic device consists of two main components, a greave or leg section 12 and a plantar or foot section 14. Both sections are contoured to the wearer's lower leg and foot by means of a molding process in which a positive mold of the wearer's foot and leg is made. The orthotic is then fabricated on the mold from multiple layers of woven reinforced and non-reinforced materials and curable plastic resin materials. The lower extremity orthotic device includes, inner surfaces 11 and 13 which, in use, are in contact with the user's leg and foot, respectively, and an outer surface 30 which, in use, is generally visible while worn by the user. Leg and foot 16 shown in dashed lines are in intimate contact with the greaves and plantar sections respectively. Disposed between greaves and plantar sections are a pair of flexible, semi-rigid, resilient plastic supports 18 which are located on the proximal and distal sides of the orthotic. Each flexible support is secured to the orthotic by means of a pair of fasteners 20. Preferably, supports 18 and fasteners 20 are secured at the inner surface of the orthotic in raised notch 22, which is adapted to receive the support and fastener therein without interfering with user comfort or the effectiveness of the orthotic. The plastic orthotic therapeutic device is secured to the wearer's leg by means of strap 24, which is preferably elastic and which also preferably includes a hook and loop pile type fastener (not shown). In order to prevent chafing, a shin pad may also be provided. On the outer surface of the orthotic is shown an example of image 28 which is visible from the perspective of the wearer or an observer. Positioned above image 28 is outer surface 30, which is comprised of a substantially transparent nylon fiber fabric layer which is embedded in the outer layer of a transparent lamination material which laminates the plastic orthotic.

In the embodiment shown, image 28 is integrally formed in the body of the orthotic by using as one of the lamination layers of the orthotic, an image bearing fabric. For laminated plastic-resin and woven fiber orthotics, specifically an ankle-foot orthosis, a positive mold of the afflicted extremity is made by processes which are generally well known in the art. With a patient's foot at approximately 90 degrees of dorsi-flexion, the extremity is encased in a wet plaster and gauze cast, which after drying forms a dry casting or negative mold of the extremity. The negative mold is removed, reassembled and filled with bulk plaster casting material. A hollow mandrel, typically a one-half inch diameter pipe, is inserted into calf-end of the bulk plaster before it hardens. The hollow mandrel facilitates the handling of and the formation of the positive mold of the extremity. The hollow mandrel includes first and second vacuum openings. After the bulk plaster casting material is completely hardened, the outer cast or negative mold is removed. The resulting positive mold is contoured and shaped to more accurately correspond to the patient's foot, and the mold is then sanded smoothed and sealed with a moisture sealant lacquer. The mandrel portion of the mold is then secured in a stand which is fitted with or otherwise associated with a vacuum apparatus.

With the mold secured in the stand, a lay-up is prepared with nonwoven plastic and woven fiber layers. First, a tubular polyvinyl alcohol casing or bag is pre-wetted on its outer surface by wrapping it in a damp towel to increase the casing's flexibility. The casing is open at both ends and is substantially longer than the mold, so as to extend beyond its calf-end or end portion. The casing is then pulled down over the toe and foot portion of the mold to beyond the calf end. The casing is pulled down to just below the first vacuum opening of the mandrel and is then sealed at the upper, toe-portion with a sealant tape. A vacuum is then applied via the second vacuum opening to evacuate any air which may be present in the polyvinyl alcohol bag. After the casing is evacuated, the end of the casing is pulled up to a point just above the first vacuum opening and a thin, tubular, woven nylon fiber fabric stockinette is rolled-down evenly over the polyvinyl alcohol casing covered mold to a point just beyond the first vacuum opening. Two successive layers of substantially thicker, tubular shaped nylon fiber fabric stockinettes are then rolled-down over the thin first nylon layer, also to a point just beyond the first vacuum opening. These layers from the base structure of this embodiment of the laminated orthotic. If desired, fiberglass or carbon-fiber reinforcing strips may be positioned at or near stress points, such as the plantar portion or the ankle portion of the orthotic at this point in the fabrication process. These strips provide additional strength and rigidity to the finished orthotic. It is important to note that each layer of material is substantially coincident with the other layers and are preferably pulled down and smoothed out so as to provide a surface that is relatively free of buckling, ridges and wrinkles.

After the initial nylon stockinette layers are in place, an image bearing fabric layer, which also has been prepared to have a generally tubular configuration, is rolled-down over the lay-up. As used herein, image means pictorial representations, line drawings, cartoons, photographs, photographic transparencies, graphic designs and insignia, as well as textured or embossed woven and non-woven fabrics and porous textured films and sheet materials. Preferably, the image bearing layer is a fabric with a cotton fiber content, and more preferably at least 50% cotton, on which the desired image or design is carried. Although cotton fiber fabrics are preferred, fabrics of other fibers such as polyester, ramie, wool, rayon and combinations of these fibers may also be used. It is essential that the fabrics used in the present invention do not add substantial weight to the orthotic and that the image or design is affixed to the fabric layer and unaffected by any solvents or chemicals used in the fabrication process. It will be appreciated that the fabric fibers will be entrapped or otherwise saturated by the plastic polyester resin or epoxy resin and that certain nonwoven fabrics and porous sheet materials may also fulfill these requirements.

After the image bearing layer is in place, an outer, thicker nylon fiber fabric layer (also tubular) is pulled down over the positive mold. This outer nylon layer completely covers the image layer but does not interfere with the visibility of the image layer in the finished orthotic device. A second polyvinyl alcohol film covering, which has also been pre-wetted in the same manner as the first, is then placed over the successive inner layers of the lay-up. The second polyvinyl alcohol covering is also sized to fit tightly over the inner layers and may, in fact, require some stretching to completely and smoothly cover the other layers. The second polyvinyl alcohol covering is pulled down to a point beyond the first vacuum opening with the end being sealed with pressure sensitive tape. This completes the lay-up of the orthotic.

The tubular shape of the outer polyvinyl alcohol film covering also facilitates introduction of a pourable plastic polyester resin or epoxy resin into the open end of the tube. With the vacuum applied, the plastic polyester or epoxy resin is worked down over and into the multiple fabric layers. In this manner, the fabric fibers of all of the layers become thoroughly embedded within or saturated by the liquid resin. Thus, as the resin hardens or cures the fabric fibers become entrapped in the plastic. In the preferred embodiments, the plastic resin used is one which when cured is clear or which is substantially colorless so as to allow the image layer to be viewed. A particularly preferred plastic resin formulation is one which provides both flexibility and rigidity, such as a mixture of 70–75% rigid polyester resin, 25–30% flexible polyester resin and 1–5% catalyst. Rigid polyester resin formulations comprise unsaturated polyester resin solutions in styrene and vinyl toluene and/or acrylate monomers, whereas flexible polyester resin formulations comprise unsaturated polyester resin solutions in styrene. In other embodiments, tinting agents, which cure transparent but colored, may be added to the plastic resin mixture to color or alter the visual effect of the image layer. Additionally, although plastic polyester or epoxy-resin materials are preferred, other low temperature thermosetting plastics materials such as phenol-formaldehyde mixtures and urea-formaldehyde mixtures may be used in the present invention.

After the plastic resin cures sufficiently, the outer polyvinyl alcohol covering is removed. The orthotic is then removed from the positive mold, the inner polyvinyl alcohol covering is removed from the inner surface of the orthotic and the orthotic is trimmed and finished for use by a patient. The resulting orthotic is one which has an image layer integrally formed within the lamination layers. The image or images on the fabric layer are clearly viewable through the outer most nylon layer which serves not only to protect the image layer but to secure that layer within the structure of the laminated orthotic device.

Figure 2:
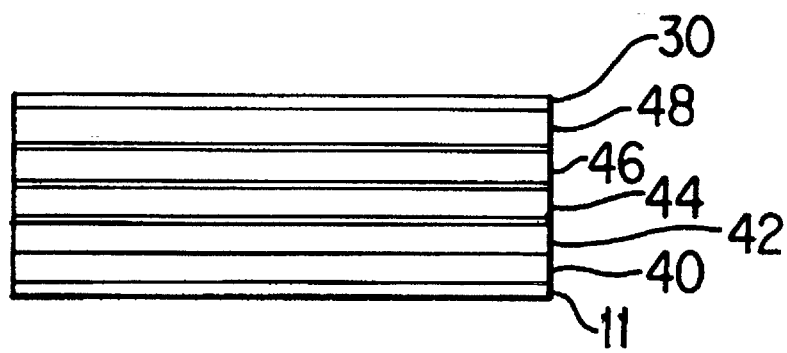
FIG. 2—Is a cross-sectional view of the ankle-foot orthosis of FIG. 1 along the line 2a–2b.

FIG. 2 is a cross-sectional view of the laminated orthotic of the present invention as shown in FIG. 1 along the lines 2a–2b. Inner surface 11 of the orthotic is substantially coincident with thin woven nylon fiber fabric layer 40. Positioned above thin layer 40 are two successive layers of substantially thicker nylon stockinette 42 and 44. These layers collectively form the base structure of the laminated orthotic. Positioned above layer 44 is image bearing layer 46 which is covered by outer nylon layer 29. Outer surface 30 forms the peripheral edge of the orthotic depicted. All of the fabric layers of the orthotic shown are substantially embedded within the plastic polyester or epoxy resin materials which form the orthotic, and thus integrally form the orthotic. It will be appreciated that additional woven or non-woven fabric layers may be added as desired with strength, weight and thickness being fundamental considerations for the finished product. It will also be appreciated that the image bearing layer is preferably situated adjacent the outer-most nylon layer, and more preferably, beneath that layer.

Figure 3:
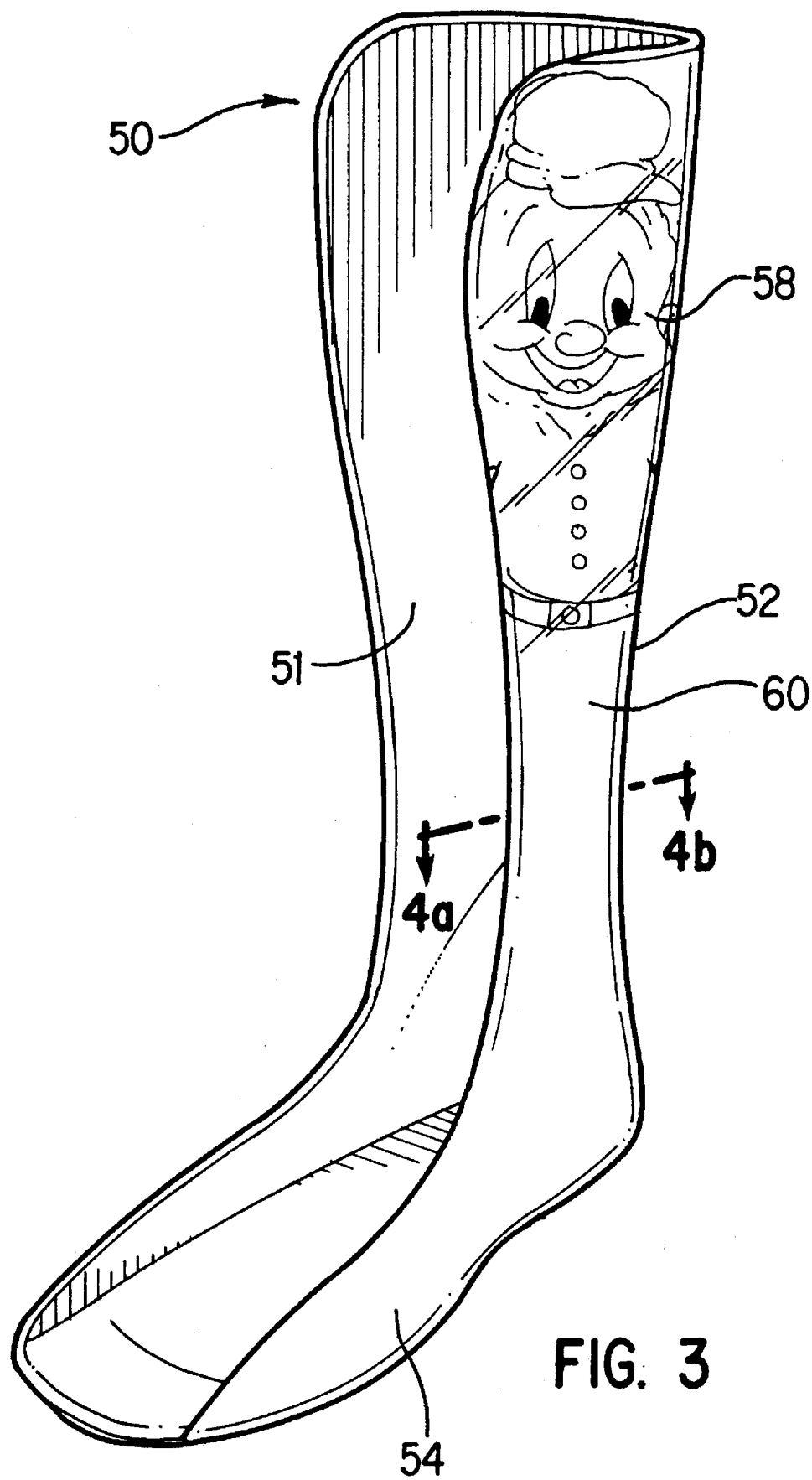
FIG. 3—Is a pictorial illustration of another preferred embodiment of the present invention.

In FIG. 3 is shown an alternate embodiment of the lightweight, plastic orthotic of the present invention generally designated by the reference numeral 50. The base structure of the orthotic is substantially composed of a lightweight, thermoplastic polymeric material which can be thermally molded and otherwise fabricated by methods well known in the art. Suitable preferred thermoplastic materials include polyethylene, polypropylene, polycarbonate and glass-reinforced vinyl. In the embodiment shown, the orthotic is of a unitary construction; however, multiple piece orthotics may also be fabricated using these materials. Greaves section 52 and plantar section 54 intersect and are connected at roughly a 90 degree angle. As in the case of the embodiment shown in FIG. 1, both sections are contoured to the wearer's lower leg and foot by means of a molding process in which a positive mold of the wearer's foot and leg is made. The lower extremity orthotic device includes an inner surface 51 which, in use, is in contact with the user's leg and foot and an outer surface 60 which, in use, is generally visible while worn by the user. The plastic orthotic therapeutic device is secured to the wearer's leg by means of a strap (not shown) which is preferably elastic and which also preferably includes a hook and loop pile type fastener (also not shown). On the outer surface of the orthotic is shown image 58 which is visible from the perspective of the wearer or an observer. Positioned above image layer 58 is the outer surface layer 60, which is comprised of a substantially transparent nylon fiber fabric layer which is embedded in the lamination material which forms the outer surface layer of the plastic orthotic. The ankle foot orthosis is worn inside shoes chosen by the user.

In the embodiment shown in FIG. 3, image 58 is integrally formed on the body of the orthotic by laminating an image bearing fabric layer to the outer surface of the thermoplastic orthotic. In these embodiments, an un-laminated, untrimmed thermoplastic orthotic is first prepared by rough-sanding its outer surface. The orthotic is prepared on a hollow mandrel having first and second vacuum openings as in the previous embodiment. A polyester based adhesive is then applied and allowed to dry. A preferred brand of polyester adhesive is a two-part mixture available from the Bostick Corporation. A tubular shaped image bearing fabric layer is then rolled down over the adhesive layer.

After the image bearing layer is in place, an outer, thicker nylon fiber fabric layer (also tubular) is pulled down over the lay-up. This outer nylon layer provides a protective outer covering to completely cover and protect the image layer and does not interfere with the visibility of the image layer. A polyvinyl alcohol film covering, which has been pre-wetted is then placed over the lay-up. The polyvinyl alcohol covering is also sized to fit tightly over the inner layers and as in the previous embodiment, may require some stretching to completely and smoothly cover the other layers. The polyvinyl alcohol covering is pulled down over the first vacuum opening, sealed with a pressure sensitive tape and the vacuum is then applied. The tubular configuration of the outer polyvinyl alcohol film covering facilitates introduction of a pourable plastic polyester resin or epoxy-resin into the open end of the tube. With the vacuum applied, the epoxy resin is worked down over and into the multiple fabric layers. In this manner, the fabric fibers of all of the layers become thoroughly embedded within or saturated by the liquid epoxy resin. Thus, the fibers become entrapped as the resin hardens or cures. In a preferred embodiment, the plastic polyester resin or epoxy resin used is one which will bond with the polyester adhesive layer and when cured is clear or which is substantially colorless so as to allow the image layer to be viewed.

After the plastic resin cures sufficiently, the outer polyvinyl alcohol covering is removed. The orthotic is then removed from the positive mold, trimmed and finished for use by a patient. The resulting orthotic is one which has a thermoplastic interior and a laminated exterior and which has an image layer integrally formed within the lamination layers.

Figure 4:
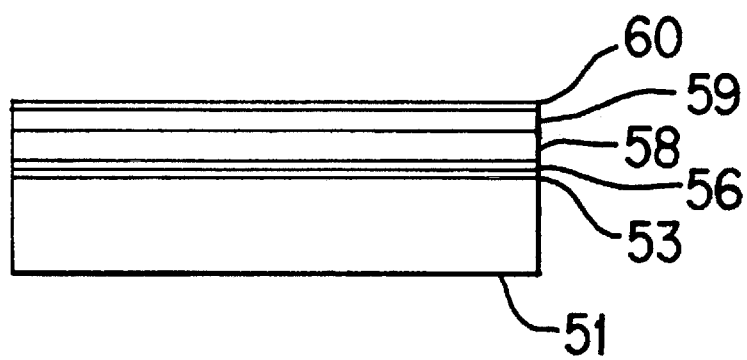
FIG. 4—Is a cross-sectional view of the ankle-foot orthosis of FIG. 3 along the line 4a–4b.

FIG. 4 is a cross-sectional view of the laminated orthotic of the present invention as shown in FIG. 3 along the lines 4a–4b. The base structure and the thermoplastic portion of the body of the orthotic is defined by inner surface 51 and abraded surface 53. Adjacent abraded surface 53 is polyester adhesive layer 56. Positioned above the adhesive layer is image bearing layer 58 which is adjacent outer nylon layer 59. Outer surface 60 forms the peripheral edge of the orthotic depicted. All of the fabric layers of the orthotic shown are permanently bonded to the thermoplastic body of the orthotic and are embedded within the plastic polyester or epoxy resin materials which form the lamination layers. Additional woven or nonwoven fabric layers may be added. Preferably the image bearing layer is situated beneath the outer-most nylon layer, although the outer-most nylon layer may be eliminated altogether in alternate embodiments.

Although the preferred embodiments of the present invention shown are orthotics of the ankle-foot type, it will be appreciated that other plastic, therapeutic orthotic and prosthetic devices can be fabricated in accordance with the teachings of the present invention. The term orthotic as used herein includes not only laminated orthotic braces such as the ankle-foot and knee-ankle-foot types, but also laminated fracture braces, laminated limb prostheses, and laminated spinal, thoracic and cervical braces.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What I claim is:

1. A preformed multilayered composite material ankle foot orthotic device having a greaves portion and a plantar portion comprising;

a substantially transparent outer layer including a thermoplastic resin;

an image bearing layer adjacent thereto, said image bearing layer comprising at least one preselected graphic image; and a base structure layer;

wherein said outer layer and said base structure layer are bonded together within a transparent thermoplastic resin and said at least one preselected graphic image is visible through said outer layer of said device.

2. The device of claim 1 wherein said layers are bonded together with a thermosetting plastic resin.

3. The device of claim 1 wherein the base structure layer comprises;

a first inner layer;

a second inner layer adjacent said first inner layer; and a third inner layer adjacent said second inner layer.

4. The device of claim 1 wherein said layers are bonded together with a thermosetting plastic resin.

5. The device of claim 4 wherein the outer layer is woven nylon and further wherein the first, second and third inner layers are woven nylon.

6. The device of claim 1 wherein the base structure is comprised of a thermoplastic material selected from the group consisting of polypropylene, polyethylene, polycarbonate and glass-reinforced vinyl.

7. The device of claim 6 further comprising a layer of polyester adhesive between said base structure and said image bearing layer.

8. The device of claim 7 which said layers are bonded together with a thermosetting plastic resin.

9. A preformed laminated ankle foot orthotic comprising;

an outer substantially transparent plastic layer;

a first outer woven fabric layer;

an image bearing layer comprising at least one preselected graphic image;

a first inner woven fabric layer;

a second inner woven fabric layer adjacent said first inner woven fabric layer;

a third inner woven fabric layer adjacent said second inner woven fabric layer; and an inner plastic layer, wherein said fabric layers are bonded together within a transparent thermoplastic resin formed from said outer and inner plastic layers and further wherein said at least one preselected graphic image is visible on the outer surface of said orthotic.

10. A preformed laminated ankle foot orthotic comprising:

an outer plastic layer;

a woven fabric layer;

an image bearing layer comprising at least one preselected image adjacent said woven fabric layer;

an adhesive layer;

a thermoplastic layer;

wherein said woven fabric layers are bonded together within a transparent thermosetting plastic resin formed from said outer plastic layer and further wherein said at least one preselected graphic image is visible on the outer surface of said orthotic.

* * * * *